(12) United States Patent
Hwang et al.

(10) Patent No.: US 9,012,679 B2
(45) Date of Patent: Apr. 21, 2015

(54) METHOD FOR CONTINUOUSLY PREPARING CARBOXYLIC ACID ESTER

(71) Applicant: China Petrochemical Development Corporation, Taipei (TW)

(72) Inventors: Jih-Dar Hwang, Taipei (TW);
Yung-Shun Kung, Taipei (TW);
Yao-Ching Tsai, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 220 days.

(21) Appl. No.: 13/651,675

(22) Filed: Oct. 15, 2012

(65) Prior Publication Data

US 2013/0303796 A1    Nov. 14, 2013

(30) Foreign Application Priority Data

May 9, 2012  (TW) .............................. 101116476 A

(51) Int. Cl.
| | |
|---|---|
| *C07C 67/03* | (2006.01) |
| *C07C 67/08* | (2006.01) |
| *C07C 69/14* | (2006.01) |
| *C07C 69/24* | (2006.01) |
| *C07C 69/40* | (2006.01) |
| *C07C 69/42* | (2006.01) |
| *C07C 69/44* | (2006.01) |
| *C07C 69/50* | (2006.01) |
| *C07C 69/54* | (2006.01) |
| *C07C 69/60* | (2006.01) |
| *C07C 69/78* | (2006.01) |
| *C07C 69/80* | (2006.01) |

(52) U.S. Cl.
CPC ................. *C07C 67/08* (2013.01); *C07C 69/14* (2013.01); *C07C 69/24* (2013.01); *C07C 69/40* (2013.01); *C07C 69/42* (2013.01); *C07C 69/44* (2013.01); *C07C 69/50* (2013.01); *C07C 69/54* (2013.01); *C07C 69/60* (2013.01); *C07C 69/78* (2013.01); *C07C 69/80* (2013.01)

(58) Field of Classification Search
CPC .. C07C 51/412; C07C 53/124; C07C 69/612; C07C 69/65; C07C 67/08
See application file for complete search history.

(56) References Cited

U.S. PATENT DOCUMENTS

| | | | | |
|---|---|---|---|---|
| 3,527,790 | A * | 9/1970 | Moundlic et al. | 560/235 |
| 4,481,146 | A * | 11/1984 | Leupold et al. | 554/170 |
| 5,536,856 | A * | 7/1996 | Harrison et al. | 554/164 |
| 5,645,696 | A * | 7/1997 | Woo et al. | 203/60 |
| 6,730,806 | B2 * | 5/2004 | Wu et al. | 560/254 |

FOREIGN PATENT DOCUMENTS

| | | |
|---|---|---|
| CN | 1332924 C | 8/2007 |
| CN | 100457263 C | 2/2009 |
| CN | 100503043 C | 6/2009 |
| JP | 2010-241765 * | 10/2010 ............. C07C 67/08 |

OTHER PUBLICATIONS

JP2010-241765, Kono, M. et al., Method for producing carboxlic acid ester, 2010, English translation, 17 pages.*

* cited by examiner

*Primary Examiner* — Yate K Cutliff
(74) *Attorney, Agent, or Firm* — Mintz Levin Cohn Ferris Glovsky and Popeo, P.C.; Peter F. Corless

(57) ABSTRACT

A method for continuously preparing a carboxylic acid ester is disclosed. In the method of the present invention, a vertical reactor is filled with a solid catalyst, a carboxylic acid and an alcohol are introduced into a lower part of the vertical reactor, esterification is performed to form an esterized mixture, the esterized mixture is output from an upper part of the vertical reactor, and distillation is performed to isolate the carboxylic acid ester. The method of the present invention is simple, easily controlled and environmental friendly, and has significantly high conversion rate and selectivity.

22 Claims, No Drawings

METHOD FOR CONTINUOUSLY PREPARING CARBOXYLIC ACID ESTER

CROSS-REFERENCES TO RELATED APPLICATIONS

This application claims under 35 U.S.C. §119(a) the benefit of Taiwanese Application No. 101116476, filed May 9, 2012, the entire contents of which is incorporated herein by reference.

FIELD OF INVENTION

The present invention relates to methods for continuously preparing carboxylic acid esters, and more particularly, to a method for continuously preparing a carboxylic acid ester from an esterification of a carboxylic acid and an alcohol.

BACKGROUND OF THE INVENTION

Carboxylic acid esters are important chemical products, and have great solubility, fluidity, non-toxicity and photostability. The carboxylic acid ester may be used as materials for organic syntheses applicable to a plasticizer, a solvent, a tobacco, a spice, an essence, a cosmetic, a medicine, a dye, a surfactant, a rubber, a plastic, a polyester resin, an adhesive, an artificial fiber or a thin film material.

A traditional carboxylic acid ester is formed from an esterification of a carboxylic acid and an alcohol catalyzed by heat or an acid. The esterification is mainly performed in a liquid phase, and after the reaction, the product is neutralized by an alkali, washed and dried to remove sulfuric acid and byproducts, so as to obtain the carboxylic acid ester. Since the carboxylic acid ester is formed from the esterification of the alcohol and the carboxylic acid in the liquid phase, the esterification is limited by the reversible equilibrium, the reaction is incomplete and thus the conversion rate of the esterification is low. In order to increase the conversion rate of the esterification, concentrated sulfuric acid is commonly used as the catalyst for the esterification. However, the concentrated sulfuric acid is a strong oxidant and a strong dehydrating agent, and thus results in side reactions such as sulfonation, oxidation, etherification or carbonization, so as to adversely affect the recovery and quality of the ester compound. Further, due to using the concentrated sulfuric acid as the catalyst, the anti-corrosion equipment is needed and increases the production cost. Moreover, after the reaction, a lot of acidic waste liquid would impair environment.

Currently, to increase the conversion rate of the esterification, Chinese Patent No. 1332924C discloses an esterification of an organic acid. The conversion rate of this esterification is more than 95%, but has the concentrated sulfuric acid as a catalyst. The acidic waste liquid would result in corrosion to equipment and in environmental pollution. Therefore, this method is not suitable for continuous productions in the industry.

U.S. Pat. No. 5,536,856 discloses an esterification method and a device for preparing a carboxylic acid ester. In this method, an ionic resin having sulphonic acid groups and/or carboxylic acid groups are used as a catalyst and stacked in a plurality of trays. The esterification is performed at a predetermined pressure, wherein the reaction of the alcohol vapor and the acid is performed via the catalyst. This method consumes a lot of alcohol and carboxylic acid, but the carboxylic acid cannot be completely conversed. Therefore, the production cost is high in this method.

Chinese Patent Application Publication No. 100457263C discloses a method for preparing a catalyst of a hetero polyacid and/or a hetero polyacid salt carried on an inorganic carrier. The catalyst is used for preparing a low-carbon carboxylic acid ester. The catalyst may reduce corrosion to equipment and environmental pollution. However, the preparation of the catalyst is complicated, the activity period of the catalyst is short, and the esterification rate is less than 90%.

Chinese Patent Application Publication No. 100503043C discloses an ionic liquid catalyst for an esterification, the preparation method and the use thereof. The ionic liquid catalyst has high reactivity and causes less environmental pollution. However, the reaction retention time is about 2 to 12 hours, and after the reaction, the ester compound is separated from the ionic liquid catalyst by gravity sedimentation. Therefore, the esterification and the purification of the ester product are time-consuming.

Hence, the sulfuric acid is used as the catalyst increasing the esterification rate, but causes corrosion to equipment and environmental pollution in the prior art.

Accordingly, there is a need to develop a method for continuously preparing a carboxylic acid ester with a high esterification rate, high selectivity and simple purification.

SUMMARY OF THE INVENTION

This invention provides a method for continuously preparing a carboxylic acid ester. In accordance with the present invention, a vertical reactor is filled with a solid catalyst, a carboxylic acid and an alcohol are introduced into a lower part of the vertical reactor to perform esterification, and after an esterized mixture is formed, the esterized mixture is distilled to isolate the carboxylic acid ester. In the esterification of the present invention, three phases of materials exist at the same time, wherein the ester product, and produced water and unreacted alcohol are gas, and the catalyst is a solid. In the esterification, the produced water is immediately removed from the reactor in the gas phase, so that the reaction is toward the ester product, and thus the carboxylic acid and the alcohol can be completely reacted.

In the method of the present invention, the boiling point of the alcohol is lower than that of water. In accordance with the present invention, the carboxylic acid and the alcohol are introduced in the same direction into the vertical reactor, such that while the gas phase contacts the liquid phase reversely in reactive distillation, the flooding prevention is achieve and the amount of continuously operation area are increased. Thus, the amount of the carboxylic acid and the alcohol introduced into the vertical reactor are significantly increased. In comparison with the prior art, the method of the present invention produces significantly more carboxylic acid ester in the continuous operation. The esterized mixture is output from an upper part of the vertical reactor, and the esterized mixture is distilled to isolate the ester product.

In accordance with present invention, the method for continuously preparing a carboxylic acid ester only needs one step esterification, and has a great conversion rate of the carboxylic acid and great selectivity. Moreover, the purification of the carboxylic acid ester is simple, and thus the method of the present invention is suitable for the continuous operation in the industry.

DETAILED DESCRIPTION OF THE PREFERRED EMBODIMENTS

In the prior art, the esterification of the carboxylic acid and the alcohol is performed in a liquid phase, such that the esterification is limited by the reversible equilibrium and the reaction is incomplete. Therefore, the concentrated sulfuric acid is used as the catalyst or multiple batches of esterification are performed for increasing the conversion rate and selectivity of the esterification.

The present invention provides a method for continuously preparing a carboxylic acid ester. In the method of the present invention, a vertical reactor is filled with a solid catalyst, a carboxylic acid and an alcohol are introduced into a lower part of the vertical reactor and pass through the solid catalyst by pumping to perform an esterification, the esterized mixture is output from an upper part of the vertical reactor after the esterification, and the esterized mixture is distilled to isolate the carboxylic acid ester. In the method of the present invention, the carboxylic acid and the alcohol are introduced in the same direction into the vertical reactor, or mixed in advance and then introduced into the vertical reactor. In the preferred embodiment of the present invention, the carboxylic acid and the alcohol are mixed, and then introduced into the lower part of the vertical reactor.

In the method of the present invention, a weight ratio of the carboxylic acid to the alcohol in the esterification is in a range of from 1:1 to 1:10, and the carboxylic acid and the alcohol are introduced into the lower part of the vertical reactor at a liquid hourly space velocity (LHSV) range of 1 to 18 hour$^{-1}$. The esterification is performed at a temperature ranging from 110 to 190° C. Then, the unreacted alcohol is recovered, the produced water is removed, and the distillation is performed to isolate the carboxylic acid ester.

In the present invention, the alcohol is a linear alcohol having 1 to 3 carbon atoms such as methanol, ethanol or n-propanol. In the esterification of the present invention, the catalyst is a solid catalyst such as an acidic ionic exchange resin.

In accordance with the present invention, the carboxylic acid may be a monocarboxylic acid and a dicarboxylic acid, wherein the monocarboxylic acid is an aliphatic carboxylic acid having 2 to 18 carbon atoms or an aromatic carboxylic acid having 7 to 10 carbon atoms. For example, the aromatic carboxylic acid is benzoic acid. In a preferred embodiment, the carboxylic acid is one selected from the group consisting of acetic acid, propionic acid, butanoic acid, pentanoic acid, hexanoic acid, hepatanoic acid, n-octanoic acid, nonanoic acid, capric acid, lauric acid, myristic acid, palmitic acid, stearic acid, methacrylic acid and benzoic acid. In the present invention, the dicarboxylic acid is a saturated aliphatic carboxylic acid having 4 to 10 carbon atoms, an unsaturated aliphatic carboxylic acid having 4 to 10 carbon atoms or an aromatic carboxylic acid having 7 to 10 carbon atoms. For example, the dicarboxylic acid may be succinic acid, glutaric acid, hexanedioic acid, azelaic acid, decanedioic acid, isophthalic acid, p-phthalic acid, fumaric aicd, maleic anhydride or phthalic acid.

In one embodiment of the present invention, the monocarboxylic acid is used, and the weight ratio of the monocarboxylic acid to the alcohol for the esterification is in a range of from 1:1 to 1:6. The monocarboxylic acid and the alcohol are mixed in advance at a temperature ranging from 30 to 80° C., and then introduced into the lower part of the vertical reactor at a liquid hourly space velocity (LHSV) range of 1 to 12 hour$^{-1}$. The esterification is performed at a temperature ranging from 110 to 190° C.

In another embodiment of the present invention, the dicarboxylic acid is used, and the weight ratio of the dicarboxylic acid to the alcohol is in a range of from 1:3 to 1:10. The dicarboxylic acid and the alcohol are mixed in advance at a temperature ranging from 50 to 75° C., and then introduced into the lower part of the vertical reactor at a liquid hourly space velocity (LHSV) range of 2 to 18 hour$^{-1}$. The esterification is performed at a temperature ranging from 120 to 190° C.

In the present invention, the esterification is simple, one step esterification and easily controlled. Furthermore, the esterification in the present invention has a high conversion rate and high selectivity.

The present invention is illustrated by, but not limited to, the following examples. A person skilled in the art can easily conceive the other advantages and effects of the present invention.

In the present invention, the ester product was analyzed by a gas chromatography. The selectivity of the esterification was calculated according to the following equation.

selectivity (mole %)=mole number of ester in the product/(mole number of the introduced carboxylic acid−mole number of carboxylic acid in the product)

In the method for continuously preparing a carboxylic acid ester of the present invention, the vertical reactor was a stainless steel tube having an inner diameter of 0.5 inch and a length of 100 cm and having a heating sleeve, and was filled with acidic cation exchange resin (AMBERLYST 70).

Method for Continuously Preparing a Monocarboxylic Acid Ester

Embodiment 1

Acetic acid and ethanol at a weight ratio of 1:2 or 1:3 were mixed at 30° C., and then introduced into the lower part of the vertical reactor at a liquid hourly space velocity (LHSV) of 3 hour$^{-1}$. The reaction was performed at 115° C. The esterized mixture was output from the upper part of the vertical reactor, and collected to be analyzed by gas photography. The acid value of the product was determined by titration, and the conversion rate and the selectivity were analyzed. The results were shown in Table 1.

Embodiments 2 and 3

The method was performed as Embodiment 1 except that the carboxylic acid and the alcohol were mixed at 30° C., and the weight ratio of the carboxylic acid and the alcohol, the introductions rate and the reaction temperatures were shown in Table 1. The analysis results of the products were shown in Table 1.

Embodiments 4 to 10

The method was performed as Embodiment 1 except that the carboxylic acid and the alcohol were mixed at 50° C., and the weight ratio of the carboxylic acid and the alcohol, the introductions rate and the reaction temperatures were shown in Table 1. The analysis results of the products were shown in Table 1.

TABLE 1

| Embodiment | Carboxylic acid | Alcohol | Temp. | Wt. ratio | LHSV | Conversion rate of acid | selectivity |
|---|---|---|---|---|---|---|---|
| Embodiment 1 | Acetic acid | Ethanol | 115° C. | 1:2 | 3 hr$^{-1}$ | 98.68% | 100% |
| | Acetic acid | Ethanol | 115° C. | 1:3 | 3 hr$^{-1}$ | 99.22% | 100% |
| Embodiment 2 | Acetic acid | 95% Ethanol | 110° C. | 1:2 | 4.5 hr$^{-1}$ | 98.18% | 100% |
| | Acetic acid | 95% Ethanol | 110° C. | 1:3 | 6 hr$^{-1}$ | 99.38% | 100% |
| | Acetic acid | 95% Ethanol | 115° C. | 1:3 | 3 hr$^{-1}$ | 98.58% | 100% |
| | Acetic acid | 95% Ethanol | 115° C. | 1:3 | 4.5 hr$^{-1}$ | 98.54% | 100% |
| Embodiment 3 | Propionic acid | Methanol | 130° C. | 1:2 | 4.5 hr$^{-1}$ | 99.13% | 100% |
| | Propionic acid | 95% Ethanol | 130° C. | 1:2 | 6 hr$^{-1}$ | 99.18% | 100% |
| Embodiment 4 | Methacrylic acid | Methanol | 145° C. | 1:4 | 6 hr$^{-1}$ | 99.31% | 100% |
| | Methacrylic acid | Ethanol | 145° C. | 1:4 | 6 hr$^{-1}$ | 99.23% | 100% |
| Embodiment 5 | Pentanoic acid | Methanol | 120° C. | 1:2 | 6 hr$^{-1}$ | 99.44% | 100% |
| | Pentanoic acid | 95% Ethanol | 145° C. | 1:3 | 6 hr$^{-1}$ | 99.27% | 100% |
| | Pentanoic acid | n-Propanol | 145° C. | 1:3 | 6 hr$^{-1}$ | 99.16% | 100% |
| Embodiment 6 | Hexanoic acid | Methanol | 145° C. | 1:3 | 6 hr$^{-1}$ | 99.72% | 100% |
| | Hexanoic acid | Methanol | 145° C. | 1:3 | 9 hr$^{-1}$ | 99.57% | 100% |
| | Hexanoic acid | Methanol | 145° C. | 1:3 | 12 hr$^{-1}$ | 99.05% | 100% |
| | Hexanoic acid | 95% Ethanol | 145° C. | 1:3 | 6 hr$^{-1}$ | 99.22% | 100% |
| Embodiment 7 | Benzoic acid | Methanol | 120° C. | 1:4 | 6 hr$^{-1}$ | 99.45% | 100% |
| | Benzoic acid | Ethanol | 120° C. | 1:4 | 6 hr$^{-1}$ | 99.10% | 100% |
| Embodiment 8 | n-Caprylic acid | Methanol | 145° C. | 1:3 | 6 hr$^{-1}$ | 99.68% | 100% |
| | n-Caprylic acid | Methanol | 145° C. | 1:3 | 9 hr$^{-1}$ | 99.54% | 100% |
| | n-Caprylic acid | 95% Ethanol | 145° C. | 1:4 | 6 hr$^{-1}$ | 99.13% | 100% |
| Embodiment 9 | Lauric acid | Methanol | 145° C. | 1:2 | 3 hr$^{-1}$ | 99.12% | 100% |
| | Lauric acid | n-Propanol | 145° C. | 1:5 | 6 hr$^{-1}$ | 99.15% | 100% |
| Embodiment 10 | Stearic acid | Methanol | 145° C. | 1:5 | 6 hr$^{-1}$ | 99.48% | 100% |
| | Stearic acid | Methanol | 145° C. | 1:5 | 9 hr$^{-1}$ | 99.23% | 100% |
| | Stearic acid | 95% Ethanol | 145° C. | 1:5 | 6 hr$^{-1}$ | 99.15% | 100% |

Method for Continuously Preparing a Dicarboxylic Acid Ester

Embodiment 11

Hexanedioic acid and methanol at a weight ratio of 1:5 were mixed at 50° C., and then introduced into the lower part of the vertical reactor at a liquid hourly space velocity (LHSV) of 6 hour$^{-1}$. The reaction was performed at 130 to 175° C., as shown in Table 2. The reaction was performed at 115° C. The esterized mixture was output from the upper part of the vertical reactor, and collected to be analyzed by gas photography. The acid value of the product was determined by titration, and the conversion rate and the selectivity were analyzed. The results were shown in Table 2.

Embodiments 12 to 14

The method was performed as Embodiment 11 except that the carboxylic acid and the alcohol were mixed at 50° C., and the weight ratio of the carboxylic acid and the alcohol, the introductions rate and the reaction temperatures were shown in Table 2. The analysis results of the products were shown in Table 2.

Embodiment 15

The method was performed as Embodiment 11, except that various carboxylic acids and ethanol at a weight ratio of 1:5 were respectively mixed, and the reaction was performed at 160° C. The analysis results of the products were shown in Table 2.

Embodiment 16

Decanedioic acid and various alcohols at a respective weight ratio of 1:5 were mixed respectively at 50° C., and introduced into the lower part of the vertical reactor at a liquid hourly space velocity (LHSV) of 6 hour$^{-1}$. The reaction temperature was 160° C. The analysis results of the products were shown in Table 2.

Embodiment 17

Fumaric acid and ethanol at a weight ratio of 1:8 were mixed, and introduced in to the vertical reactor at the rate shown in Table 2. The reaction temperature was 145° C. The analysis results of the products were shown in Table 2.

Embodiment 18

Maleic anhydride and methanol at a weight ratio of 1:5 were mixed at 50° C., and introduced in to the vertical reactor at the rate shown in Table 2. The reaction temperature was 145° C. The analysis results of the products were shown in Table 2.

Embodiment 19

Maleic anhydride and ethanol at a weight ratio of 1:5 were mixed at 65° C., and introduced in to the vertical reactor at the rate shown in Table 2. The reaction temperature was 145° C. The analysis results of the products were shown in Table 2.

Embodiment 20

Phthalic acid and various alcohols at a respective ratio of 1:7 were respectively mixed at 55° C., and introduced in to the vertical reactor at a liquid hourly space velocity (LHSV) of 3 hour$^{-1}$. The respective reaction temperature was shown Table 2. The analysis results of the products were shown in Table 2.

TABLE 2

| Embodiment | Carboxylic acid | Alcohol | Temp. | Wt. ratio | LHSV | Conversion rate of acid | selectivity |
|---|---|---|---|---|---|---|---|
| Embodiment 11 | Hexanedioic acid | Methanol | 130° C. | 1:5 | 6 hr$^{-1}$ | 100% | 99.00% |
| | Hexanedioic acid | Methanol | 145° C. | 1:5 | 6 hr$^{-1}$ | 100% | 99.47% |
| | Hexanedioic acid | Methanol | 160° C. | 1:5 | 6 hr$^{-1}$ | 100% | 99.64% |
| | Hexanedioic acid | Methanol | 175° C. | 1:5 | 6 hr$^{-1}$ | 100% | 99.59% |
| Embodiment 12 | Hexanedioic acid | Methanol | 145° C. | 1:5 | 9 hr$^{-1}$ | 100% | 99.32% |
| | Hexanedioic acid | Methanol | 145° C. | 1:5 | 12 hr$^{-1}$ | 100% | 99.25% |
| | Hexanedioic acid | Methanol | 160° C. | 1:5 | 12 hr$^{-1}$ | 100% | 99.33% |
| | Hexanedioic acid | Methanol | 160° C. | 1:5 | 15 hr$^{-1}$ | 100% | 99.05% |
| | Hexanedioic acid | Methanol | 175° C. | 1:5 | 15 hr$^{-1}$ | 100% | 99.18% |
| | Hexanedioic acid | Methanol | 175° C. | 1:5 | 18 hr$^{-1}$ | 100% | 98.82% |
| Embodiment 13 | Glutaric acid | Methanol | 145° C. | 1:5 | 6 hr$^{-1}$ | 100% | 98.87% |
| | Glutaric acid | Methanol | 160° C. | 1:5 | 6 hr$^{-1}$ | 100% | 99.67% |
| Embodiment 14 | Succinic acid | Methanol | 145° C. | 1:5 | 6 hr$^{-1}$ | 100% | 99.59% |
| | Succinic acid | Methanol | 160° C. | 1:5 | 6 hr$^{-1}$ | 100% | 99.67% |
| Embodiment 15 | Hexanedioic acid | Ethanol | 160° C. | 1:5 | 6 hr$^{-1}$ | 100% | 99.03% |
| | Glutaric acid | Ethanol | 160° C. | 1:5 | 6 hr$^{-1}$ | 100% | 99.02% |
| | Succinic acid | Ethanol | 160° C. | 1:5 | 6 hr$^{-1}$ | 100% | 99.18% |
| Embodiment 16 | decanedioic acid | Methanol | 160° C. | 1:5 | 6 hr$^{-1}$ | 100% | 99.13% |
| | decanedioic acid | Ethanol | 160° C. | 1:5 | 6 hr$^{-1}$ | 100% | 98.34% |
| Embodiment 17 | Fumaric acid | Ethanol | 145° C. | 1:8 | 3 hr$^{-1}$ | 100% | 99.34% |
| | Fumaric acid | Ethanol | 145° C. | 1:8 | 6 hr$^{-1}$ | 100% | 99.26% |
| Embodiment 18 | Maleic anhydride | Methanol | 145° C. | 1:5 | 6 hr$^{-1}$ | 96.41% | 100% |
| | Maleic anhydride | Methanol | 145° C. | 1:5 | 9 hr$^{-1}$ | 96.92% | 100% |
| Embodiment 19 | Maleic anhydride | Ethanol | 145° C. | 1:5 | 9 hr$^{-1}$ | 96.76% | 100% |
| | Maleic anhydride | Ethanol | 145° C. | 1:5 | 12 hr$^{-1}$ | 96.24% | 100% |
| Embodiment 20 | Phthalic acid | Methanol | 120° C. | 1:7 | 3 hr$^{-1}$ | 100% | 99.31% |
| | Phthalic acid | n-Propanol | 145° C. | 1:7 | 3 hr$^{-1}$ | 100% | 98.39% |

Accordingly, the method for continuously preparing a carboxylic acid ester of the present invention has short the reaction time without using concentrated sulfuric acid as a catalyst, so as to prevent the limitation of the reversible equilibrium in the liquid phase, and thus to improve the conversion rate of the carboxylic acid and the alcohol and the selectivity of the ester. Moreover, the carboxylic acid ester is easily isolated from the product, and the production efficacy is thus increased.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A method for continuously preparing a carboxylic acid ester, comprising the steps of:
   introducing a carboxylic acid and an alcohol in the same direction into a lower part of a vertical reactor to perform an esterification for forming an esterized mixture, wherein the vertical reactor is filled with a solid catalyst; and
   outputting the esterized mixture from an upper part of the vertical reactor.

2. The method of claim 1, further comprising the step of distilling the esterized mixture output from the vertical reactor for isolating the carboxylic acid ester and water.

3. The method of claim 1, wherein before introducing the carboxylic acid and the alcohol, the carboxylic acid and the alcohol are mixed.

4. The method of claim 3, wherein a weight ratio of the carboxylic acid to the alcohol is in a range of from 1:1 to 1:10.

5. The method of claim 1, wherein the carboxylic acid and the alcohol are introduced into the lower part of the vertical reactor at a liquid hourly space velocity range of 1 to 18 hour$^{-1}$.

6. The method of claim 1, wherein the esterification is performed at a temperature in a range of from 110 to 190° C.

7. The method of claim 1, wherein the carboxylic acid is an aliphatic carboxylic acid having 2 to 18 carbon atoms or an aromatic carboxylic acid having 7 to 10 carbon atoms.

8. The method of claim 1, wherein the alcohol is a linear alcohol having 1 to 3 carbon atoms.

9. The method of claim 8, wherein the alcohol is methanol, ethanol or n-propanol.

10. The method of claim 1, wherein the solid catalyst is an acidic cation exchange resin.

11. The method of claim 1, wherein the carboxylic acid is a monocarboxylic acid.

12. The method of claim 11, wherein the monocarboxylic acid is an aliphatic carboxylic acid having 2 to 18 carbon atoms or an aromatic carboxylic acid having 7 to 10 carbon atoms.

13. The method of claim 11, wherein a weight ratio of the carboxylic acid to the alcohol is in a range of from 1:1 to 1:6.

14. The method of claim 11, wherein the carboxylic acid and the alcohol are introduced into the lower part of the vertical reactor at a liquid hourly space velocity range of 1 to 12 hour$^{-1}$.

15. The method of claim 11, wherein before introducing the carboxylic acid and the alcohol, the carboxylic acid and the alcohol are mixed at a temperature ranging from 30 to 80° C.

16. The method of claim 11, wherein the esterification is performed at a temperature in a range of from 110 to 190° C.

17. The method of claim 1, wherein the carboxylic acid is a dicarboxylic acid.

18. The method of claim 17, wherein the dicarboxylic acid is one selected from the group consisting of a saturated aliphatic carboxylic acid having 4 to 10 carbon atoms, an unsaturated aliphatic carboxylic acid having 4 to 10 carbon atoms and an aromatic carboxylic acid having 7 to 10 carbon atoms.

19. The method of claim 17, wherein a weight ratio of the dicarboxylic acid to the alcohol is in a range of from 1:3 to 1:10.

20. The method of claim 17, wherein the dicarboxylic acid and the alcohol are introduced into the lower part of the vertical reactor at a liquid hourly space velocity range of 2 to 18 hour$^{-1}$.

21. The method of claim 17, wherein before introducing the dicarboxylic acid and the alcohol, the dicarboxylic acid and the alcohol are mixed at a temperature ranging from 50 to 75° C.

22. The method of claim 17, wherein the esterification is performed at a temperature in a range of from 120 to 190° C.

* * * * *